United States Patent [19]

von Werner et al.

[11] Patent Number: 5,068,415

[45] Date of Patent: Nov. 26, 1991

[54] PROCESS FOR THE PREPARATION OF HALOGENOTETRAFLUOROPROPIONIC ACID

[75] Inventors: Konrad von Werner, Halsbach; Anton Probst, Burgkirchen, both of Fed. Rep. of Germany

[73] Assignee: Hoechst Aktiengesellschaft, Frankfurt am Main, Fed. Rep. of Germany

[21] Appl. No.: 93,309

[22] Filed: Sep. 4, 1987

Related U.S. Application Data

[62] Division of Ser. No. 939,544, Dec. 9, 1986, abandoned.

[30] Foreign Application Priority Data

Dec. 11, 1985 [DE] Fed. Rep. of Germany ....... 3543710

[51] Int. Cl.$^5$ ..................... C07C 51/285; C07C 53/21
[52] U.S. Cl. ................................... 562/541; 562/605; 570/135; 570/137; 570/157

[58] Field of Search ................. 562/541, 605

[56] References Cited

FOREIGN PATENT DOCUMENTS

3606174 8/1987 Fed. Rep. of Germany ...... 562/541
43-29129 12/1968 Japan ................................. 562/541

*Primary Examiner*—Vivian Garner

[57] ABSTRACT

The halogenotetrafluoropropionic acid 3-iodotetrafluoropropionic acid of the formula $ICF_2CF_2COOH$, it is prepared by reacting iodine, tetrafluoroethylene and ethylene in a one-pot reaction under specific conditions, reacting the resulting compound $ICF_2CF_2CH_2CH_2I$ with a base in order to eliminate hydrogen iodide and oxidizing the compound $ICF_2CF_2-CH=CH_2$ thus obtained to give 3-iodotetrafluoropropionic acid. The halogenotetrafluoropropionic acid is an advantageous starting compound for the preparation of valuable unsaturated compounds containing functional groups.

1 Claim, No Drawings

PROCESS FOR THE PREPARATION OF HALOGENOTETRAFLUOROPROPIONIC ACID

CROSS REFERENCE TO RELATED APPLICATION

This application is a division of our copending application, U.S. Ser. No. 939,544, filed Dec. 9, 1986, now abandoned.

The invention relates to a new 3-halogenotetrafluoropropionic acid. It also relates to processes for the preparation of this propionic acid and to its use.

3-Halogenotetrafluoropropionic acids, namely 3-bromotetrafluoropropionic and 3-chlorotetrafluoropropionic acid, and also pentafluoropropionic acid are already known (cf. Chemical Abstracts, volume 70, 1969, Abstract No. 77,334 q).

They are prepared by a thermal addition reaction, elimination of hydrogen halide acid from the addition compound and subsequent oxidation to give the corresponding propionic acid; the equations below, in which X represents bromine, are intended to illustrate this:

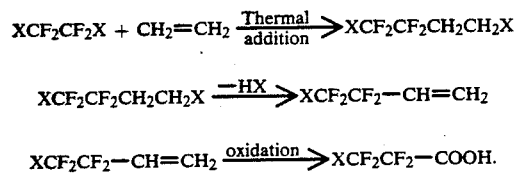

Since the bromine atom and, in particular, the chlorine and fluorine atom are relatively firmly attached and are therefore more or less slow to react, the known 3-halogenotetrafluoropropionic acids are largely unsuitable as starting materials for the preparation of compounds containing an advantageous functional group instead of the halogen atom. 3-Iodotetrafluoropropionic acid, which would not exhibit the disadvantages mentioned, is not yet known.

A process for the preparation of the compounds $ICF_2CF_2CH_2CH_2I$ and $ICH_2CH_2CF_2CF_2CH_2CH_2I$ by a thermal addition reaction between 1,2-diiodotetrafluoroethane ($ICF_2CF_2I$) and ethylene is disclosed in U.S. Pat. No. 3,016,407. In this reaction $ICF_2CF_2I$ and $CH_2=CH_2$ are heated under pressure at a temperature of 180° to 220° C., and the desired compound is isolated from the resulting reaction product. If the process is carried out discontinuously, it is recommended that $ICF_2CF_2I$ should first be prepared by reacting $I_2$ and $C_2F_4$ at a temperature of about 150° C., and the reaction of $ICF_2CF_2I$ with ethylene should be carried out subsequently in a second reaction stage. It is emphasised expressly in the U.S. patent mentioned that the preparation of $ICF_2CF_2CH_2CH_2I$ in a single-stage process, that is to say by simultaneous reaction of iodine, tetrafluoroethylene and ethylene, is not possible, because considerable amounts of unwanted 1,2-diiodoethane ($ICH_2CH_2I$) would then be obtained.

It has now been found, surprisingly, that the compound $ICF_2CF_2CH_2CH_2I$ can be prepared in good yields in a one-pot process from iodine, tetrafluoroethylene and ethylene without the formation in appreciable amounts of the compound $ICH_2CH_2I$. It has also been found that the compound $ICF_2CF_2-CH=CH_2$ can be obtained from the butane compound mentioned by eliminating hydriodic acid, and that the corresponding propionic acid can be obtained from the compound $ICF_2CF_2-CH=CH_2$ by oxidation.

The invention therefore relates to 3-iodotetrafluoropropionic acid: $ICF_2CF_2COOH$. The process, according to the invention, for the preparation of this acid comprises reacting iodine, tetrafluoroethylene and ethylene in a molar ratio of 1:(1.2–2):(1–1.2) at a temperature of 170° to 200° C. in a one-pot reaction, and isolating from the resulting reaction product the compound 1,4-diiodo-1,1,2,2-tetrafluorobutane ($ICF_2CF_2CH_2CH_2I$), reacting this butane compound with a base in order to eliminate hydrogen iodide (HI), and isolating the compound 1-iodo-1,1,2,2-tetrafluoro-3-butene ($ICF_2CF_2-CH=CH_2$) from this reaction product, reacting this butene compound with an oxidizing agent in order to convert it into the corresponding propionic acid, and isolating 3-iodo-2,2,3,3-tetrafluoropropionic acid ($ICF_2CF_2COOH$) from this reaction product. The process according to the invention is in accord with the equations (1) to (3) below:

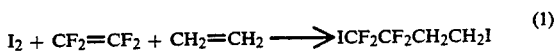

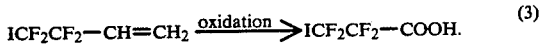

The reaction shown in equation (1) is possible and also results in a high yield of the desired compound if the conditions according to the invention, indicated above, are maintained. An excess of tetrafluoroethylene greater than the 1.2 to 2 mol indicated favors the formation of $ICF_2CF_2I$ and $ICH_2CH_2(CF_2CF_2)_nI$, while an excess of ethylene greater than the 1.2 mol indicated favors the formation of $ICH_2CH_2I$ and $ICH_2CH_2CF_2CF_2CH_2CH_2I$ (n=an integer>1). The reaction time required at the reaction temperature of 170° to 200° C. indicated is about 5 to 20 hours, depending on the temperature chosen, i.e. the reaction time for virtually complete conversion is about 5 hours if the reaction temperature is 200° C. and is about 20 hours if the reaction temperature is 170° C. Clearly, a pressure corresponding to the compounds present will prevail during the reaction according to the invention. At the start of the reaction it is about 40 to 70 bar and it decreases as the reaction proceeds. The desired compound is isolated from the reaction product obtained. This isolation is preferably effected by fractional distillation of the liquid reaction product. If the reaction conditions according to the invention are maintained, not only is a high yield of the desired compound ($ICF_2CF_2CH_2CH_2I$) obtained, but also only very few by-products, such as diiodoethane ($ICH_2CH_2I$), or none at all, are formed.

In the reaction according to equation (2), hydrogen iodide is eliminated by means of a base. The nature of the base is not critical. Examples of suitable bases are alkali metal hydroxides, such as potassium hydroxide and sodium hydroxide, alkoxides, such as sodium methylate and potassium methylate, or tertiary amines. In a preferred embodiment of equation (2), the compound $ICF_2CF_2CH_2CH_2I$ is reacted with at least a stoichiometric amount of potassium hydroxide or sodium hydroxide in the form of an approximately 10 to 60% strength by weight aqueous solution at a temperature of 20° to 100° C., preferably 50° to 90° C. (the reaction can be followed by means of the amount of potassium iodide or sodium iodide, respectively, formed), and the desired compound ($ICF_2CF_2$—$CH$=$CH_2$) is isolated from the reaction product by phase separation or fractional distillation. It is advantageous to employ an excess (in comparison with the stoichiometric amount) of potassium hydroxide or sodium hydroxide, specifically an excess of about 0.5 to 2 mol. It has been found that the reaction described, with alkali metal hydroxide solution, proceeds particularly advantageously and is accelerated if phase transfer catalysts, for example in the form of tetraalkylammonium salts, are present. Examples of suitable tetraalkylammonium salts are tetrabutylammonium bromide, tricetylmethylammonium chloride, dioctyldimethylammonium chloride and dodecyltrimethylammonium bisulfate. The amount of phase transfer catalyst is about 0.1 to 5 mol %, preferably 0.5 to 2 mol %, relative to the amount of compound $ICF_2CF_2CH_2CH_2I$ employed. In the reaction described, with alkali metal hydroxide, it is preferable to add the phase transfer catalyst to the alkali metal hydroxide solution and to meter in the compound $ICF_2CF_2CH_2CH_2I$ to the initially taken alkali metal hydroxide solution containing the phase transfer catalyst, at the temperature indicated.

The oxidation according to equation (3) is carried out by means of an oxidizing agent. The nature of the oxidizing agent is not critical. Examples of suitable oxidizing agents are potassium permanganate, chromium trioxide, chromic sulfuric acid, osmium tetroxide, ozone and peroxoacetic acid. In a preferred embodiment of the equation (3), the compound $ICF_2CF_2$—$CH$=$CH_2$ is reacted with at least a stoichiometric amount of potassium permanganate in the form of an approximately 10 to 40% strength aqueous solution or suspension at a temperature of 5° to 50° C., preferably 10° to 25° C. (the reaction can be followed by means of consumption of oxidizing agent), and the desired 3-iodotetrafluoropropionic acid is isolated from the reaction product by fractional distillation after removing the manganese dioxide formed and acidification. It is preferable to employ a slight excess (in comparison with the stoichiometric amount) of potassium permanganate, specifically an excess of about 0.01 to 0.1 mol. The equation below is intended to illustrate the oxidation described with potassium permanganate:

3 $ICF_2CF_2$—$CH$=$CH_2$ + 10 $KMnO_4$ → 3 $ICF_2CF_2$—$CO_2K$ + 10 $MnO_2$ + 3 $K_2CO_3$ + $KOH$ + 4 $H_2O$

It has been found that the oxidation described, using an aqueous solution of potassium permanganate, affords particularly high yields of the desired propionic acid if phase transfer catalysts, for example in the form of quaternary ammonium or phosphonium salts, are present. The tetraalkylammonium salts indicated above and the corresponding phosphonium salts constitute suitable phase transfer catalysts in this case too. The amount of phase transfer catalyst is about 0.5 to 5 mol %, preferably 1 to 3 mol %, relative to the amount of compound $ICF_2CF_2$—$CH$=$CH_2$ employed. In the reaction indicated above it is preferable to employ a procedure in which the aqueous potassium permanganate solution containing the added phase transfer catalyst is initially taken, and the compound $ICF_2CF_2$—$CH$=$CH_2$ is metered in at the temperature indicated. The reaction rate can be controlled conveniently by means of the rate of metering at which the olefin is fed to the stirred mixture of potassium permanganate, water and phase transfer catalyst. The heat of reaction can readily be controlled by cooling. At the end of the reaction, the 3-iodotetrafluoropropionic acid is present in the form of its potassium salt, together with manganese dioxide. The potassium salt can be separated off from the manganese dioxide ($MnO_2$) by hot filtration, and the free propionic acid can be isolated by evaporating the filtrate to dryness, adding sulfuric acid, preferably concentrated sulfuric acid, and distillation. 3-Iodo-tetrafluoropropionic acid ($ICF_2CF_2$-COOH) is a colorless liquid which slowly turns pink in the light and crystallizes at room temperature. It has a boiling point of 78° C. at 13 mbar.

3-Iodotetrafluoropropionic acid is a valuable starting compound for the preparation of other $\Omega$-iodo compounds into which functional groups can be introduced at the terminal iodine atom by known processes. Thus, the new 3-halogenotetrafluoropropionic acid is an advantageous starting compound for the preparation of unsaturated comonomers containing functional groups for the production of electrolysis membranes. Thus it is possible, for example, to obtain the compound $FSO_2$—$(CF_2)_3$—$O$—$CF$=$CF_2$ from $ICF_2CF_2COOH$ by means of known methods. This compound, and its advantageous use for the preparation of polymers for the production of electrolysis membranes, is known.

The invention will now be illustrated in greater detail by means of an example. The nuclear magnetic resonance data indicated in the example relate to deuterochloroform solutions (Standard: tetramethylsilane for $^1H$-NMR and trifluorofacetic acid for $^{19}F$-NMR. Signals having a positive sign are at a lower field, compared with the standard resonance).

Preparation of 1,4-diiodo-1,1,2,2-tetrafluorobutane

A 250 ml shaking autoclave is charged with 76.2 g (0.3 mol) of iodine, cooled to −76° C. and freed from oxygen by being evacuated and filled with argon three times. After a further evacuation, 50 g (0.5 mol) of tetrafluoroethylene and 9.0 g (0.32 mol) of ethylene are condensed successively into the autoclave. The autoclave is then heated to 180° C. in the course of 5 hours and is shaken at this temperature for 15 hours. In the course of this, the pressure falls from 58 bar to 14 bar. After cooling to room temperature and releasing the pressure, 121.3 g of a liquid product are obtained which, according to nuclear magnetic resonance analysis ($^{19}F$-NMR and $^1H$-NMR) has the following composition (in mol %):

0.9% of $ICH_2CH_2I$
6.5% of $ICF_2CF_2I$
3.0% of $ICF_2CF_2H$
80.1% of $ICF_2CF_2CH_2CH_2I$,
4.3% of $I(CF_2CF_2)_2CH_2CH_2I$,
5.2% of $ICH_2CH_2CF_2CF_2CH_2CH_2I$.

Fractional distillation in vacuo of this mixture gives 88.5 g of $ICF_2CF_2CH_2CH_2I$ (liquid of boiling point 72°/15 mbar; turns violet in light). The yield is 77.3%, relative to the iodine employed. Nuclear magnetic resonance data:

$^{19}F$-NMR: 18.8 ppm ($CF_2I$), −29.3 ppm ($CF_2$).
$^1H$-NMR: 3.24 ppm ($CH_2I$, triplet), 2.74 ppm ($CH_2$, multiplet).

Preparation of 1-iodo-1,1,2,2-tetrafluoro-3-butene 200 g (5.0 mol) of NaOH, 1 liter of demineralized water and 7.5 g (0.025 mol) of $[(C_8H_{17})_2N(CH_3)_2]^+Cl^-$ as phase transfer catalyst are initially placed in a 2.5 liter glass flask equipped with a dropping funnel, a stirrer, a thermometer and an upright 20 cm packed column. The mixture is heated to 90° C., and 819 g (2.14 mol) of $ICF_2CF_2CH_2CH_2I$ are added dropwise slowly, with stirring, to the heated mixture, the latter being kept at the boil. The take-off reflux ratio at the head of the column is adjusted to 1:1 and a mixture of fluorine compounds and water is collected continuously in an ice-cooled receiver until no further organic constituents pass over (bottom temperature at the conclusion 105° C.; reaction time: 2.5 hours). The distillate is extracted by shaking with water, and the organic phase is dried with sodium sulfate. 451 g of crude product are obtained, and fractional distillation of this gives 335 g (1.319 mol) of $ICF_2CF_2-CH=CH_2$ (boiling point 86° to 88° C./980 mbar) and 105 g (0.275 mol) of starting compound. The yield is 70.7%, relative to $ICF_2CF_2CH_2CH_2I$ which has reacted. Nuclear magnetic resonance data:

$^{19}$F-NMR: 18.2 ppm ($CF_2I$), −30.0 ppm ($CF_2$).
$^1$H-NMR: 5.78–6.09 ppm ($CH=CH_2$, multiplet).

Preparation of 3-iodo-tetrafluoropropionic acid 383.9 g (2.43 mol) of potassium permanganate and 1 liter of demineralized water are placed in a 2.5 liter glass flask equipped with dropping funnel, stirrer and thermometer, 5.0 g (0.016 mol) of $[(C_8H_{17})_2N(CH_3)_2]^+Cl^-$ are added, with stirring, as phase transfer catalyst, and the mixture is stirred for 10 minutes. 187 g (0.7365 mol) of $ICF_2CF_2-CH=CH_2$ are then added dropwise in the course of 3 hours, with vigorous stirring and external cooling, the internal temperature being kept between 15° and 20° C. The mixture is then stirred for a further 4 hours at room temperature and is heated to 70° C., and the manganese dioxide formed is filtered off by means of a heatable pressure filter. The manganese dioxide is stirred with 1 liter of boiling water and is again filtered off. The combined filtrates are concentrated to dryness on a rotary evaporator under reduced pressure. The residue is transferred to a distillation apparatus, and 500 ml of concentrated sulfuric acid are added cautiously (initial foaming caused by evolution of $CO_2$). Vacuum distillation gives 290.6 g (72.5% yield) of pure 3-iodotetrafluoropropionic acid (boiling point 78° C./13 mbar): a colorless liquid which slowly turns pink in light and crystallizes at room temperature.

Elemental analysis:
C: 13.1%, H: 0.5%, F: 27.7%, I: 46.8%
(calculated: C: 13.25%, H: 0.37%, F: 27.95%, I: 46.66%).

Nuclear magnetic resonance data:
$^{19}$F-NMR: 18.0 ppm ($CF_2I$), −32.9 ppm ($CF_2$)
$^1$H-NMR: 12.5 ppm ($CO_2H$).

We claim:
1. A process for the preparation of 3-iodotetrafluoropropionic acid, which comprises:
reacting iodine, tetrafluoroethylene and ethylene in a molar ratio of 1:(1.2–2):(1–1.2) at a temperature of 170° to 200° C. in a one-pot reaction, and isolating from the resulting reaction product the compound 1,4-diiodo-1,1,2,2-tetrafluorobutane,
the 1,4-diiodo-1,1,2,2-tetrafluorobutane reacting with at least a stoichiometric amount of potassium hydroxide or sodium hydroxide in the form of an approximately 10 to 60% strength by weight aqueous solution at a temperature of 20° to 100° C. and in the presence of a phase transfer catalyst in an amount of 0.1 to 5 mol %, relative to the amount of 1,4-diiodo-1,1,2,2-tetrafluorobutane, to eliminate hydrogen iodide, and isolating 1-iodo-1,1,2,2-tetrafluoro-3-butene from this reaction product,
oxidizing the 1-iodo-1,1,2,2,-tetrafluoro-3-butene with at least a stoichiometric amount of potassium permanganate in the form of an approximately 10 to 40% strength by weight aqueous solution or suspension at a temperature of 5° to 50° C. and in the presence of a phase transfer catalyst in an amount of 0.5 to 5 mol %, relative to the amount of 1-iodo-1,1,2,2,-tetrafluoro-3-butene in order to convert the 1-iodo-1,1,2,2,-tetrafluoro-3-butene to the corresponding propionic acid, and
isolating 3-iodo,2,2,3,3-tetrafluoropropionic acid from the reaction product.

* * * * *